Figure 1:
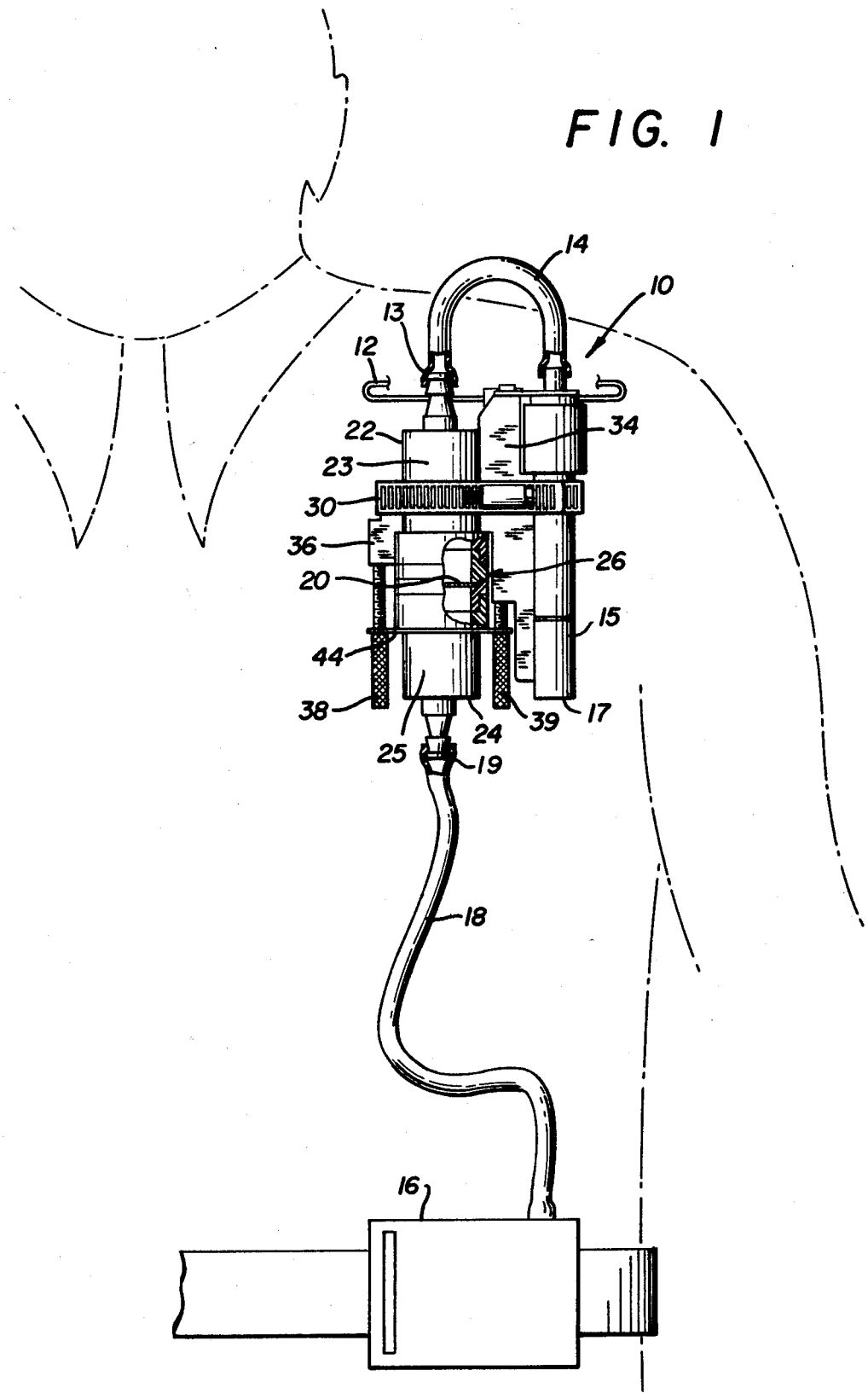

United States Patent [19]

Jugle et al.

[11] 4,178,794

[45] Dec. 18, 1979

[54] ENVIRONMENTAL SAMPLING DEVICE

[75] Inventors: Lawrence C. Jugle, Niagara Falls; Emil R. Inderbitzen, Eggertsville; Paul W. McDaniel, Port Chester, all of N.Y.

[73] Assignee: Union Carbide Corporation, New York, N.Y.

[21] Appl. No.: 882,190

[22] Filed: Feb. 28, 1978

[51] Int. Cl.$^2$ .................. G01N 1/22; B01D 46/10
[52] U.S. Cl. ........................... 73/28; 55/270; 55/467; 55/503; 55/511; 73/421.5 R
[58] Field of Search ............... 55/270, 495, 503, 511, 55/467; 73/28, 421.5 R

[56] References Cited

U.S. PATENT DOCUMENTS

| 2,059,017 | 10/1936 | Nickle | 55/503 |
| 2,974,749 | 3/1961 | Donguy | 55/511 |
| 3,561,253 | 2/1971 | Dorman | 55/270 |
| 3,598,532 | 8/1971 | Adams et al. | 55/270 |
| 3,765,247 | 10/1973 | Riggs | 73/421.5 R |
| 3,886,800 | 6/1975 | Boehringer | 73/421.5 R |

OTHER PUBLICATIONS

F. H. Vonderheiden & J. W. Knauber, "A Technique for the Direct X-Ray Diffraction Analysis for Quartz of Air-Borne Dust Collected on Silver Membranes", 1969.

J. LeRoux and Davey, "Proposed Standard Methotiology for Evaluation", American Industrial Hygiene Association Journal, vol. 34 Issue 9, pp. 409–417, 1973.

J. Leroux, "Preparation of Thin Dust Coatings for their Analysis by X-Ray Emission and Diffraction", Occupational Health Division, Dept. of National Health and Welfare, Reprinted from Staub Reinhaltung der Luft (German Edition) vol. 29, No. 4, 1969.

"Industrial Ventilation" Committee on Industrial Ventilation, P. O. Box 453, Lansing, Michigan 48902, U.S.A. American Conference of Governmental Industrial Hygienists, Section 9, 1968.

Primary Examiner—David L. Lacey
Attorney, Agent, or Firm—Frederick J. McCarthy, Jr.

[57] ABSTRACT

Device for collecting air-borne dust samples on a membrane in an even distribution which enables X-ray diffraction analysis of the collected samples.

1 Claim, 7 Drawing Figures

ENVIRONMENTAL SAMPLING DEVICE

The present invention is directed to an apparatus for collecting air-borne dust samples, particularly quartz dust samples. More particularly the present invention is directed to an apparatus for collecting dust samples and providing an even distribution of the collected sample on a membrane such that X-ray diffraction measurements can be made directly from the dust sample collected on the membrane.

It has been previously known to collect dust samples on a membrane by passing air-borne dust for X-ray diffraction analysis through a sampling device having two chambers separated by a screen-supported silver membrane.

This device reportedly achieves an even distribution of dust due to the use of a chamber upstream of the membrane. However, it has been found that it is important to provide further improvement in the evenness of the distribution of the dust sample to enable effective X-ray diffraction analysis and to provide an efficient arrangement for removal of the membrane from the sampling device.

It is therefore an object of the present invention to provide an apparatus for collecting dust samples on a membrane to achieve an even distribution of the dust samples on the membrane and enable ready removal of the dust ladden membrane for direct X-ray diffraction analysis.

Other objects will be apparent from the following description and claims taken in conjunction with the drawing wherein FIG. 1 shows the sampling device of the present invention.

Figure 1A:
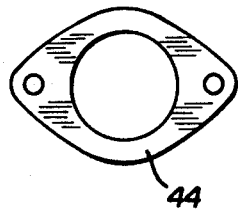

FIG. 1(a) shows a plan view of the ring support member shown in elevation in FIG. 1.

Figure 2B:
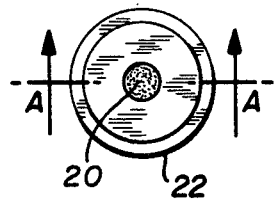
Figure 3B:
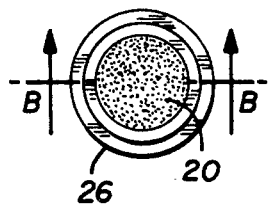
Figure 2A:
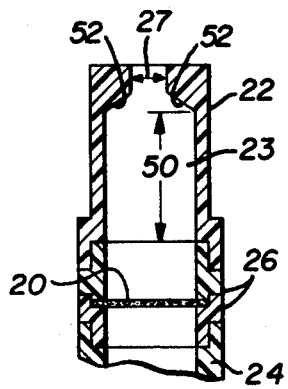
Figure 3A:
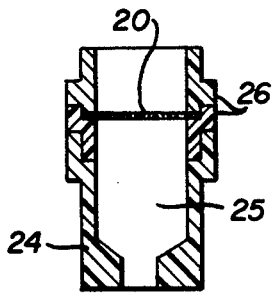
Figure 4:
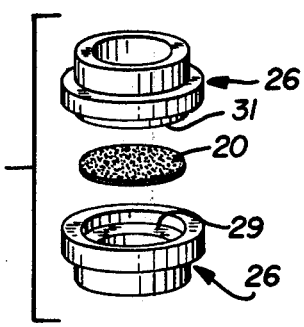

FIGS. 2(a) and 2(b) show respectively a sectional elevation view and plan view of the upper portion of the device of FIG. 1, FIGS. 3(a) and 3(b) show respectively, a sectional elevation view and plan view of the lower portion of the device of FIG. 1 and FIG. 4 shows the membrane holding arrangement of the device of FIG. 1.

With reference to FIG. 1, the sampling device of the present invention indicated generally at 10, is shown attached to a worker's outer garment in the upright, i.e. vertical, position shown, by suitable means such as the safety pin arrangement indicated at 12.

The sampling device 10 communicates through a flexible, e.g. rubber tube 14 and fitting 13 to a conventional cyclone 15, e.g. MSA CYCLONE ASSEMBLY CATALOG No. 456228 which separates the respirable particulates from the non-respirable particulates in the air sample which enters the cyclone at 17. A conventional portable air pump 16, e.g. MSA model G DIAPHRAM PUMP CATALOG No. 456059, usually attached to the worker's belt, communicates with the sampling device 10 by means of flexible, e.g. rubber tube 18 and fitting 19 and coventionally operates to cause a dust laden air sample to be drawn through cyclone 15 and deposited on membrane 20. Sampling defice 10 comprises an upper housing 22, a lower housing 24 and a cassette 26 for supporting membrane 20 between the chamber's 23 and 25 of housing 22 and 24. Housings 22 and 24 are suitably made of a machinable pore-free thermosetting resin, such as Delrin* a thermoplastic resin [—(OCH$_2$—)n] as described in "Handbook of Material Trade Names"-Zimmerman and Levine Supplement III Industrial research Service Inc. (1960) as is cassette 26, which comprises two separate, snugly fitting portions 29 and 31 as shown in FIG. 4. Sampling device 10 and cyclone 15 are held in place by adjustable metal strap 30 and maintained upright by plexiglass support plate 34 and mount 36 to which the sampling device 10 is secured by screws 38,39 and ring 44 shown more clearly in FIG. 1(a). The above-described arrangement established a gas-tight seal for the communicating chambers 23 and 25 and supportably holds membrane 20 in place without any other support for membrane 20; the avoidance of any obstruction to the flow of air through membrane 20 and chambers 23 and 25 enables the collection of an evenly distributed dust sample on membrane 20 due to avoidance of turbulence in the vicinity of membrane 20.

*Trademark of E. I. duPont de Nemours Co.

With reference to FIG. 2, upper housing 22 containing chamber 23 is configured to establish laminar flow in the dust laden air stream entering through passage 27. To this end, it is important that the length 50 of chamber 23 in the upstream housing 22 is about 13 times the diameter of entering passageway 27 and the inner diameter of chamber 23 is about 6.75 times the diameter of passageway 27, additionally, the upper portions of chamber 23 are sloped, e.g., about 30°, as indicated at 52. Lower, down-stream housing 24 shown in FIG. 3, is similarly configured, having precisely the same inner diameter, chamber 25 being about 35% shorter in length than chamber 23 of upper housing 22. Cassette 26 is tightly held between housings 22 and 24 and the inner surfaces of the cassette 26 are flush with the inner surfaces of housings 22 and 24 thus providing a smooth sided passageway within the sampling device 10. With reference to FIG. 4, the snugly fitting and closely contacting parts 29 and 31 of cassette 26 hold membrane 20 securely and forcibly in place; membrane 20 is a suitably a conventional silver membrane of sintered particles having a thickness of about 0.002 inch and about 25 mm in diameter. Such membranes are known in the art and are commercially available, e.g. from Selor Flotronics Membrane, Spring House, Pa.

In operation, due to the smooth sided and unobstructed configuration of chambers 23 and 25 and the inner surfaces of cassette 26, vertically downward laminar air flow is established in the vicinity adjacent both sides of membrane 20 and a highly uniform deposit of dust is collected on membrane 20. After collection, the cassette 26 is removed and sent to a laboratory where the dust sample is weighed and measured directly by known conventional X-ray diffraction techniques and the results compared to a suitable standard. The membrane is removed from the cassette only for this X-ray diffraction testing and weighing and a fresh cassette can be immediately inserted in sampling device 10 in place of the one being tested.

Paticular advantages of the present invention are that a repeatable method is provided for the deposition of respirable dust on a suitable membrane to afford convenient X-ray diffraction analysis; gravity assists rather than interferes in the sample deposition; contamination-free removal of the sample bearing membrane in the field, and installation of a new membrane for the next sample is easily accomplished; convenient on the job "fixing" of the sample and e.g. using collodion, and secure transporting of completed samples for analysis is enabled; any possible interference of a backup screen or frit on the even distribution of the sample on the membrane is avoided.

What is claimed is:

1. In combination with a portable means for providing a flow of dust laden air, a portable sampling device adapted for attachment to a worker's apparel for receiving a flow of dust laden air from said portable means and collecting air-borne dust samples therefrom, said portable sampling device comprising a first housing member having an inlet for receiving a dust laden air sample, a chamber communicating with said inlet and an annular recessed end portion opposite said inlet said chamber having a length which is about 13 times the diameter of said inlet and an inner diameter which is about 6.75 times the diameter of said inlet; a second housing member arranged adjacent to and in-line with said first housing member having an annular recessed portion adjacent the recessed portion of said first housing member to define an annular groove, a chamber within said second housing member having a length about 35% shorter than the length of the chamber of said first housing member communicating with the chamber of said first housing member, and an outlet; a closely engaging pair of ring-shaped members arranged in said annular groove; and a dust collecting membrane being supportably engaged only peripherally between said ring-shaped members, the diameter of the inner surfaces of said chambers and said ring-shaped members being essentially the same so as to provide a smooth surfaced passageway.

* * * * *